US00PP18835P2

(12) United States Plant Patent
Robacker et al.

(10) Patent No.: US PP18,835 P2
(45) Date of Patent: May 27, 2008

(54) ***ABELIA* PLANT NAMED 'PLUM SURPRISE'**

(50) Latin Name: ***Abelia* hybrid**
Varietal Denomination: Plum Surprise

(75) Inventors: Carol Robacker, Peachtree, GA (US); Sloane M. Scheiber, Ocoee, FL (US)

(73) Assignee: University of Georgia Research Foundation, Inc., Athens, GA (US)

( * ) Notice: Subject to any disclaimer, the term of this patent is extended or adjusted under 35 U.S.C. 154(b) by 8 days.

(21) Appl. No.: 11/595,035

(22) Filed: Nov. 9, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Wendy C. Haas
(74) *Attorney, Agent, or Firm*—Greenlee Winner and Sullivan, P.C.

(57) ABSTRACT

A new and distinct *Abelia* hybrid which is characterized by compact, weeping mounded growth habit, red purple autumn and winter foliage color, and small leaves which are retained during heat and drought stress in summer and cold stress in winter.

3 Drawing Sheets

Figure 1:
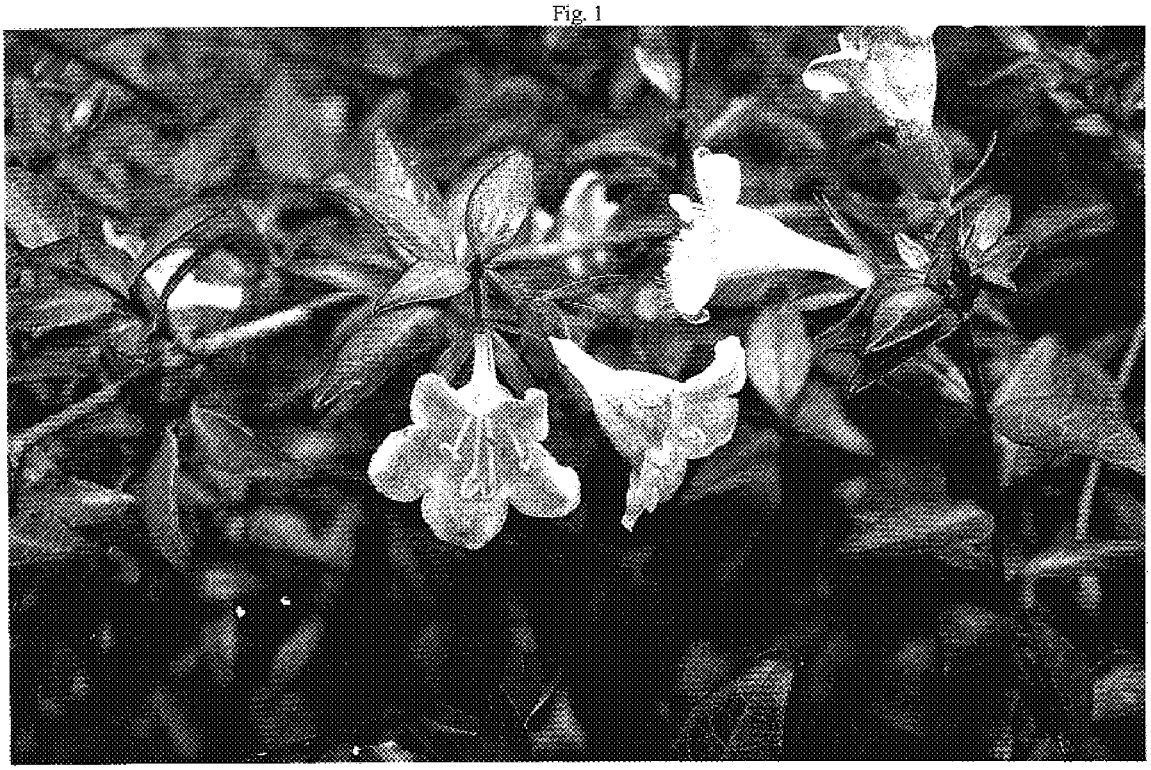

Botanical classification: *Abelia* hybrid.
Varietal denomination: 'Plum Surprise'.

BACKGROUND OF THE INVENTION

The present invention relates to a new and distinct cultivar of the ornamental flowering shrub *Abelia,* hereinafter referred to by the varietal denomination 'Plum Surprise'. 'Plum Surprise' originated from an interspecific cross made in 1998 between the cultivars 'Edward Goucher' (unpatented) and 'Francis Mason' (unpatented). 'Edward Goucher' is a purple-flowered cultivar that was derived from an interspecific cross between *Abelia×grandifolia* and *A. parvifolia* (*schumanii*) and was released in 1911. 'Francis Mason' is a variegated cultivar of *Abelia×grandifolia* that was grown in New Zealand in the 1970s. Seeds from this cross were sown in 1999, and five seedlings were obtained. These seedlings were planted in a field plot in Griffin in the fall of 1999 and were evaluated for three years for flowering and foliage characteristics, plant form and height, cold hardiness and drought tolerance. Plant 99-7-1 was selected among these plants, and assigned the name 'Plum Surprise'.

'Plum Surprise' forms a weeping, spreading mound. A 4-year old, unpruned, field grown plant measured 92 cm tall and 171 cm wide. Check cultivars including 'Compacta' (unpatented) (195×240 cm), 'Golden Glow' (unpatented) (175×211 cm), 'Francis Mason' (132×137 cm), 'Little Richard' (unpatented) (165×244 cm) and 'Rose Creek' (unpatented) (142×198 cm) were all significantly larger.

Foliage color in March and April is a yellow-green with scattered red/purple leaves. In late spring, the majority of the foliage becomes a bright emerald green, remaining green throughout the summer. In mid-October, the foliage begins to turn red/purple and as autumn progresses, the outer/upper shoots and leaves become red/purple with the underlying foliage remaining bright green. By December, the foliage becomes glossy, and the purple color intensifies. As winter progresses most of the leaves turn burgundy. Leaves of 'Plum Surprise' are very small, approximately 11 mm at the widest point and 20 mm in length.

The flowering of 'Plum Surprise' is sparse and scattered as 2 to 4 blooms per inflorescence. Individual flowers appear white, but on close examination have a purple blush with a pale yellow throat.

'Plum Surprise' performs well in a container under nursery conditions. The foliage cascades down over the pot, making an attractive appearance in both form and color.

Laboratory evaluations of cold hardiness in Griffin, Ga. during the winter of 2003–04 revealed a mid-winter hardiness of −15 to −18° C., similar to the check cultivars ('Francis Mason' and 'Rose Creek'). Field observations of plants grown in Griffin, Ga. (USDA Zone 7b) from 2000 to 2006 revealed no cold damage and the plant retained in 80 to 90% of its leaves in the winter. Plants grown in Blairsville, Ga. (USDA Zone 7a) from 2003 to 2006 have occasionally had moderate shoot dieback through all plants survived.

Although *Abelia* is known for its heat and drought tolerance, leaf drop is a usual characteristic of such stressed plants. 'Plum Surprise' showed exceptional heat and drought tolerance. The summer of 2002 was very hot and dry in Griffin, Ga., with a rainfall total from May 1$^{st}$ to August 31$^{st}$ of 26.4 cm and 24 days reaching at least 32° C. The test plot was not irrigated, and the check cultivars of 'Compacta', 'Francis Mason', 'Golden Glow' and 'Little Richard' lost 50 to 80% of their foliage, whereas 'Plum Surprise' retained nearly all of its foliage, and remained an attractive plant.

SUMMARY OF THE INVENTION

Plants of cultivar 'Plum Surprise' have not been observed under all possible environmental conditions. The phenotype may vary somewhat with variations in environment such as light-intensity, temperature and cultural conditions, however without any variance in genotype.

The following characteristics have been consistently observed and, to the best knowledge of the inventor, their combination forms the unique characteristics of 'Plum Surprise' as a new and distinct cultivar.

1. Short, weeping habit, unlikely any available cultivars known to the inventors.
2. Purple-burgundy fall and winter foliage.
3. Very small leaves.

4. Exceptional heat and drought tolerance, with excellent retention of leaves in both the winter and summer.

The inventor is not aware of any similar weeping habit cultivars available for direct comparison with 'Plum Surprise'.

'Plum Surprise' is readily propagated through cuttings. Six-inch cuttings, collected in August, root well in peat-perlite mix under mist. Asexual propagation since 2001 has shown that the unique characteristics of this new cultivar are stable and reproduced true to type in successive generations.

BRIEF DESCRIPTION OF PHOTOGRAPHS

The accompanying colored photographs illustrate the characteristics of the new cultivar, showing the colors as true as it is reasonably possible to obtain in colored reproductions of this type. Colors in the photograph may differ from the color values listed in the detailed botanical description which accurately describes the colors of the new *Abelia*.

FIG. 1. Flowers and foliage on 4-year old plant, taken Jun. 3, 2005.

Figure 2:
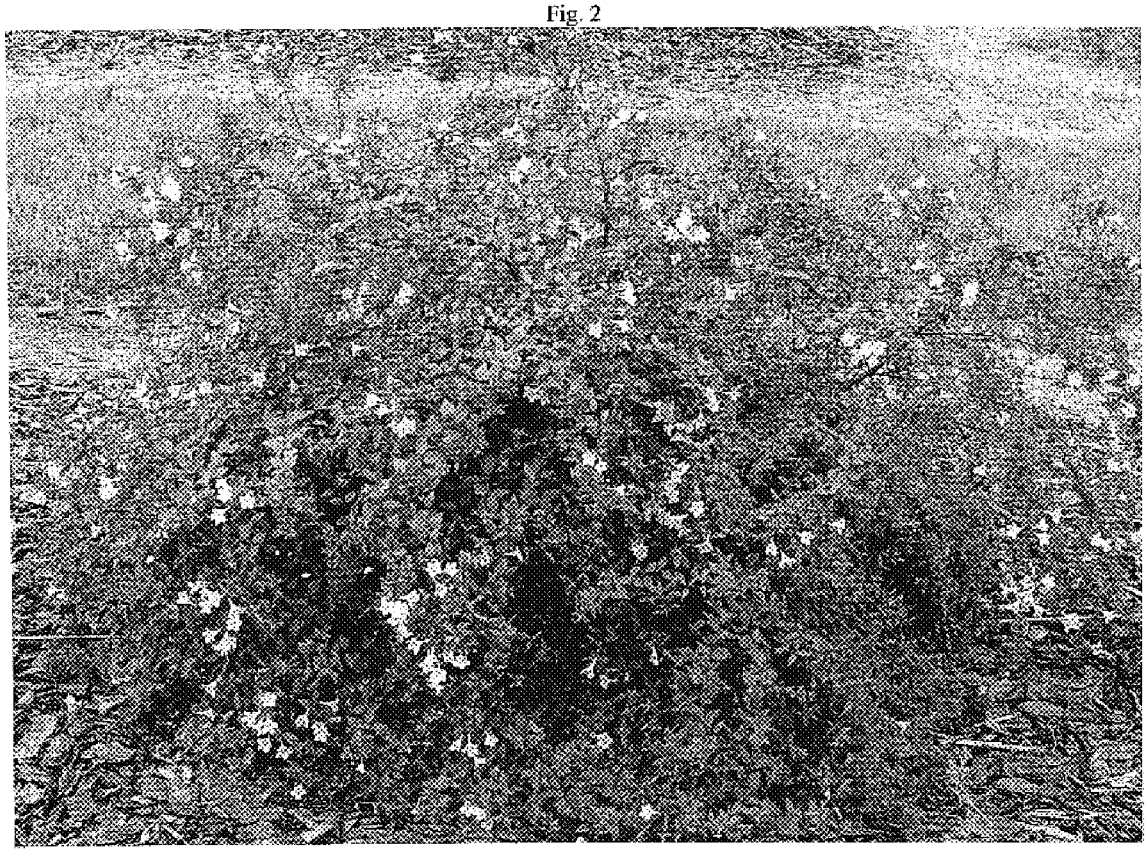

FIG. 2. 4-year old plant showing flowering habit and summer color, taken Aug. 25, 2003.

Figure 3:
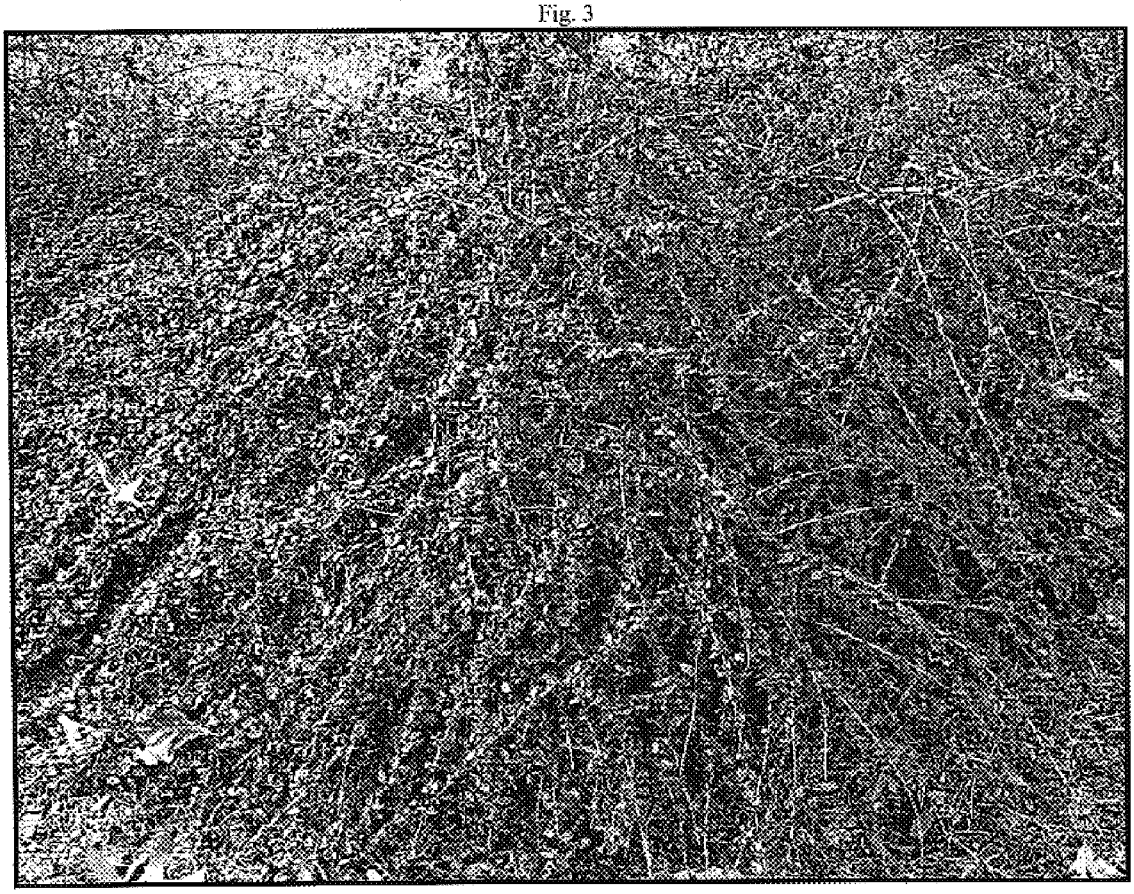

FIG. 3. 4-year old plant showing weeping habit and fall color, with the red purple leaves and underlying green foliage, taken Nov. 19, 2004.

DETAILED BOTANICAL DESCRIPTION

The botanical description of 'Plum Surprise' is based on 4-year old plants growing in the field in Griffin, Ga. (USDA Zone 7b). Colors are based on The Royal Horticultural Color Chart (2001). Unless otherwise indicated, measurements, averages based on 10 to 20 samples, were taken in July/August of 2005.

The plant has a weeping, spreading mound habit with fine texture of branching, attaining an average growth height of 92 cm and width of 171 cm after 4-years unpruned growth in the field.

Current year stems are round, 2 mm in diameter, covered with minute fine hairs, some curved, and are Greyed-Red 181A in color. The stems show some longitudinal cracks, usually starting close to leaf axils. The average internode length is 23 mm.

Older stems are round, up to 9 to 13 mm in diameter and vary from Greyed-Orange 175C to Greyed-Yellow 161D with Greyed-Orange 166A striations with maturation. Exfoliation occurs on the mature stems.

The vegetative buds are opposite, imbricate, lanceolate in shape, 3 mm long by 1 mm wide, glabrous, with 3 scales Greyed-Purple 185B in color. There are 2 vegetative buds at each node, at 45° to the stem.

The mature leaf is 19.8 mm long by 10.7 mm wide. It is simple acuminate in shape with an acute apex, obtuse base and sparsely crenate margin. The upper and lower surfaces are covered in very short hairs, almost dots, with longer hairs along the midvein and outer edges. They are moderately waxy, up to 0.5 mm thick and opposite in clusters on the stem. The venation is mostly attenuate and the main veins are Green 139D in color.

The emerging leaves (March) are Yellow-Green 144A on upper and lower surfaces, with Greyed-Orange 165A at the apex. In summer (July) the leaves are Green 137C on the upper and Green 139D on the lower surface. In the fall the upper surface varies from Green 137B to Greyed-Orange 172B to Greyed-Orange 175A, with lower surfaces, Green 138B to Greyed-Yellow 161D to Green 139D. In winter the majority of the leaves have the upper surface varying from Greyed-Purple 186A to Greyed-Purple N186C to Greyed-Purple 187B, with lower surface Green 138C or 138B. A few leaves remain Green 137A on upper and lower surfaces.

The petiole is slightly curved and flattened on the upper surface, 3.5 mm in length and 1 mm in diameter, sparse to glabrous and Yellow-Green 144B in color.

The flower buds are elongated teardrop in shape, 14 mm long by 5 mm wide, covered in short glandular hairs and Purple N77B to Red-Purple 63B in color. The buds show from early summer to frost.

The inflorescence is a loose panicle, 3 cm by 3 cm with 2 to 4 flowers per inflorescence. At emergence the outside tips are Purple-Violet N81C with Violet 84B funnel and Violet 84C inside. At full bloom the outside is Violet 84B, the funnel Violet 84D and inside Violet 84C.

The peduncle has a few very short hairs, and is Greyed-Orange 172B in color.

The flower is funnel shaped with an 8 mm tube, gamopetalous, slightly zygomorphic. The whole flower is 2 cm by 1.6 cm with five, 6 mm lobes. The margin is entire with the edges slightly curved back. The outside has short glandular hairs. The inside has short hairs with longer hairs on the anterior petal lobes down into funnel. The color of the upper surface is Violet 84C, with the throat netted with Yellow-Orange 15D. The lower surface is Violet 84B at the tip and Violet 84D in the funnel.

The pedicels are 1 mm long, with bracteoles and a few short hairs, and Greyed-Orange 172B in color.

There are 4 to 5 sepals, some with 4 plus 1 cleft. They are 6 mm long by 1.5 mm wide, oblanceolate in shape with acute apex, equal slightly alternate base and usually entire margin with occasional cleft. They have very short stubby hairs, smooth texture and are Greyed-Red 181B with a Green 141D background on both upper and lower surfaces.

There are 4 stamens.

The anther is 1.5 mm long by 1 mm wide and Greyed-Yellow 160D in color.

The filament is petalostemonous, approximately half way down the filament, 15 mm long and 0.3 mm wide with many fine hairs. The color is White N155B.

The pollen color is White N155B.

The pistil is monostylus, free in shape, 20 mm long by 1.5 mm wide with sparse hairs.

The stigma is circular, slightly domed in shape, with clear short hair-like structures and is Orange-White 159D in color.

The style is tubular in shape, 17 mm long with sparsely scattered hairs, and White 155D in color.

The single, inferior ovary is oval in shape with no pubescence.

The fruit is an achene, a grooved cylindrical capsule in shape, 4 mm long and 1.5 mm wide with 1 carpel. The color matures from Greyed-Red 181B and Green 141D to Greyed-Orange 174A.

No insect or disease problems have been noted in container plants maintained outside the greenhouse, or in field grown plants.

We claim:

1. A new and distinct cultivar of *Abelia* plant named 'Plum Surprise', substantially as illustrated and described.

* * * * *